US009785745B2

(12) United States Patent
Bravi et al.

(10) Patent No.: US 9,785,745 B2
(45) Date of Patent: Oct. 10, 2017

(54) SYSTEM AND METHOD FOR PROVIDING MULTI-ORGAN VARIABILITY DECISION SUPPORT FOR EXTUBATION MANAGEMENT

(71) Applicant: Ottawa Hospital Research Institute, Ottawa (CA)

(72) Inventors: Andrea Bravi, Ottawa (CA); Christophe L. Herry, Fournier (CA); Andrew J. E. Seely, Ottawa (CA)

(73) Assignee: Ottawa Hospital Research Institute, Ottawa (CA)

( * ) Notice: Subject to any disclaimer, the term of this patent is extended or adjusted under 35 U.S.C. 154(b) by 53 days.

(21) Appl. No.: 14/680,519

(22) Filed: Apr. 7, 2015

(65) Prior Publication Data
US 2015/0213221 A1    Jul. 30, 2015

Related U.S. Application Data

(63) Continuation of application No. PCT/CA2013/050811, filed on Oct. 25, 2013.
(60) Provisional application No. 61/757,578, filed on Jan. 28, 2013, provisional application No. 61/718,871, filed on Oct. 26, 2012.

(51) Int. Cl.
| | |
|---|---|
| G01N 33/48 | (2006.01) |
| G06F 19/00 | (2011.01) |
| A61B 5/083 | (2006.01) |
| A61M 16/04 | (2006.01) |
| G06G 7/58 | (2006.01) |
| A61B 5/01 | (2006.01) |
| A61B 5/0402 | (2006.01) |
| A61B 5/145 | (2006.01) |

(52) U.S. Cl.
CPC .......... *G06F 19/3431* (2013.01); *A61B 5/083* (2013.01); *A61M 16/04* (2013.01); *G06F 19/345* (2013.01); *G06F 19/3437* (2013.01); *A61B 5/01* (2013.01); *A61B 5/0402* (2013.01); *A61B 5/14542* (2013.01); *A61M 2205/60* (2013.01)

(58) Field of Classification Search
CPC .......... G06F 19/18; G06F 19/22; G06F 19/24
See application file for complete search history.

(56) References Cited

U.S. PATENT DOCUMENTS

| | | |
|---|---|---|
| RE41,236 E | 4/2010 | Seely |
| 8,473,306 B2 | 6/2013 | Seely |
| 2007/0179369 A1 | 8/2007 | Baker, Jr. |
| 2010/0057490 A1 | 3/2010 | Kocis et al. |
| 2011/0184303 A1 | 7/2011 | Skinner et al. |

FOREIGN PATENT DOCUMENTS

| | | |
|---|---|---|
| WO | WO 2009/098627 A1 | 8/2009 |
| WO | WO 2014/063256 A1 | 5/2014 |

OTHER PUBLICATIONS

Brendemuhl, S.; Supplementary European search report from corresponding European Application No. 13849369.7; search completed Apr. 26, 2016.
Yang K.L. et al.; "A Prospective Study of Indexes Predicting the Outcome of Trials of Weaning from Mechanical Ventilation"; New England Journal of Medicine; May 23, 1991; vol. 324; pp. 1445 to 1450.
Esteban, A. et al.; "Effect of Spontaneous Breathing Trial Duration on Outcome of Attempts to Discontinue Mechanical Ventilation"; American Journal of Respiratory and Critical Care Medicine; 1999; vol. 159; pp. 512 to 518.
Esteban, A. et al.; "A Comparison of Four Methods of Weaning Patients from Mechanical Ventilation"; New England Journal of Medicine; Feb. 9, 1995; vol. 332; pp. 345 to 350.
Esteban, A. et al.: "Noninvasive Positive-Pressure Ventilation for Respiratory Failure after Extubation"; New England Journal of Medicine; Jun. 10, 2004; vol. 350; pp. 2452 to 2460.
Nevins, M.L. et al.; "Predictors of Outcome for Patients with COPD Requiring Invasive Mechanical Ventilation"; CHEST Journal; vol. 119; pp. 1840 to 1849.
Demling, R.H. et al.; "Incidence and morbidity of extubation failure in surgical intensive care patients"; Critical care medicine; Jun. 1998; vol. 16, No. 6.
Task Force of the European Society of Cardiology the North American Society of Pacing Electrophysiology; "Heart Rate Variability: Standards of Measurement, Physiological Interpretation, and Clinical Use," Circulation; Mar. 1996; pp. 1043 to 1065; vol. 93.
Cerutti, S. et al.; "Recent Advances in Heart Rate Variability Signal Processing and Interpretation"; IEEE Transactions on Biomedical Engineering; Jan. 2006; vol. 53, No. 1.
Epstein, S. K. et al.; "Effect of Failed Extubation on the Outcome of Mechanical Ventilation"; Chest Journal; 1997; vol. 112; pp. 186 to 192.
Zhang, P. Z. et al. ; "Respiration Response Curve Analysis of Heart Rate Variability" ; IEEE Transactions on Biomedical Engineering; Apr. 1997; vol. 44.
Bravi, A. et al.: "Review and classification of variability analysis techniques with clinical applications"; Biomedical Engineering OnLine; Oct. 20, 2011; 10-90.
Frutos-Vivar, F. et al.: "Risk factors for Extubation Failure in Patients Following a Successful Spontaneous Breathing Trial"; CHEST Journal; 2006; vol. 130; pp. 1664 to 1671.
Goldman, J. M. et al.; "Neural Network Analysis of Physiologic Waveforms"; in Proceedings of the Annual International Conference of the IEEE Engineering in Medicine and Biology Society; 1991; pp. 1660 to 1661; vol. 13.
Dasta, J. F. et al. ; "Daily cost of an intensive care unit day: The contribution of mechanical ventilation"; Critical Care Medicine; 2005; vol. 33, No. 6; pp. 1266 to 1271.
Mueller et al.; "Predicting Extubation Outcome in Preterm Newborns: A Comparison of Neural Networks with Clinical Expertise and Statistical Modeling"; Pediatric Research; 2004; vol. 56, No. 1; pp. 11 to 18.
Bodnar, K.; International PCT Search Report from corresponding PCT Application No. PCT/CA2013/050811; search completed Feb. 19, 2014.

*Primary Examiner* — Eric S Dejong
(74) *Attorney, Agent, or Firm* — Brett J. Slaney; Blake, Cassels & Graydon LLP

(57) ABSTRACT

A decision support system is provided for the management of extubation in intensive care unit patients. Based on multi-organ variability analysis of physiological signals, the proposed system transforms acquired waveforms into clinical information such as the risk of failing extubation and the probability of passing extubation. Furthermore, a variety of mechanisms are provided for displaying the extracted information to support a clinician's decisions.

22 Claims, 9 Drawing Sheets

FIG. 3

SYSTEM AND METHOD FOR PROVIDING MULTI-ORGAN VARIABILITY DECISION SUPPORT FOR EXTUBATION MANAGEMENT

CROSS-REFERENCE TO RELATED APPLICATIONS

This application is a continuation of International PCT Application No. PCT/CA2013/050811 filed on Oct. 25, 2013 which claims priority from U.S. Provisional Application Nos. 61/718,871 filed Oct. 26, 2012; and 61/757,578 filed Jan. 28, 2013, all incorporated herein by reference.

TECHNICAL FIELD

The following relates to systems and methods for providing multi-organ variability decision support for extubation management.

DESCRIPTION OF THE RELATED ART

Intensive care unit (ICU) patients are commonly unable to autonomously sustain breathing, and therefore may require intubation to receive mechanically assisted ventilation. When patients improve, to determine readiness for extubation, a patient is periodically required to perform a test referred to as a spontaneous breathing trial (SBT), which includes breathing for about 30 minutes with minimal assistance from a mechanical ventilator. When a patient is deemed to be able to tolerate this test, the patient is extubated.

It has been shown that between 5% and 20% (with a mean of 15%) of the time, a patient fails extubation, i.e. requires re-intubation within 48 hours (see: (1) Yang, K. L. & Tobin, M. J. A prospective study of indexes predicting the outcome of trials of weaning from mechanical ventilation. *New England Journal of Medicine* 324, 1445-1450 (1991); (2) Esteban, A. et al. Effect of spontaneous breathing trial duration on outcome of attempts to discontinue mechanical ventilation. *American journal of respiratory and critical care medicine* 159, 512-518 (1999); and (3) Nevins, M. L. & Epstein, S. K. Predictors of outcome for patients with COPD requiring invasive mechanical ventilation. *CHEST Journal* 119, 1840-1849 (2001)).

It has also been shown that failed extubation is associated with increased ICU mortality, increased length in hospital stay, increased number of tracheostomies, increased costs, longer terms and increased need for rehabilitation care (see: (4) Demling, R. H., Read, T., Lind, L. J., Flanagan, H. L. & others Incidence and morbidity of extubation failure in surgical intensive care patients. *Critical care medicine* 16, 573 (1988); (5) Esteban, A. et al. A comparison of four methods of weaning patients from mechanical ventilation. *New England Journal of Medicine* 332, 345-350 (1995); (6) Epstein, S. K., Ciubotaru, R. L. & Wong, J. B. Effect of failed extubation on the outcome of mechanical ventilation. *Chest* 112, 186-192 (1997); and (7) Esteban, A. et al. Noninvasive positive-pressure ventilation for respiratory failure after extubation. *New England Journal of Medicine* 350, 2452-2460 (2004)).

SUMMARY

A decision support system to improve prediction of extubation failure is therefore needed (see: (8) Frutos-Vivar, F. et al. Risk factors for extubation failure in patients following a successful spontaneous breathing trial. *CHEST Journal* 130, 1664-1671 (2006)). It has been found that extubation management can be improved through the prompt identification of readiness for safe extubation, which would be associated with reduced length of stay and costs (see: (9) Dasta, J. F., McLaughlin, T. P., Mody, S. H. & Piech, C. T. Daily cost of an intensive care unit day: The contribution of mechanical ventilation*. *Critical care medicine* 33, 1266-1271 (2005)).

A decision support system is therefore provided for the management of extubation in ICU patients. Based on multi-organ variability analyses of physiological signals, the proposed system transforms acquired waveforms into clinical information such as the risk of failing extubation and the probability of passing extubation. Furthermore, a variety of mechanisms are provided for displaying the extracted information to support a clinician's decisions. The system may be used to both decrease extubation failure by identifying when risk is high, as well as expedite extubation when risk is low, thus improving extubation outcomes, patient outcomes and costs of care.

In one aspect, there is provided a method comprising: obtaining a variability data set indicative of a degree and character to which at least one patient parameter changes over an interval of time; generating at least one statistical model using the variability data set; and creating at least one decision support index from the statistical model.

In other aspects, there is provided computer readable media, electronic devices, and systems configured for performing the method.

BRIEF DESCRIPTION OF THE DRAWINGS

Embodiments will now be described by way of example only with reference to the appended drawings wherein:

FIG. 3 is a screen shot of an example of an SBT synoptic report including a decision support portion;

DETAILED DESCRIPTION

Figure 1:
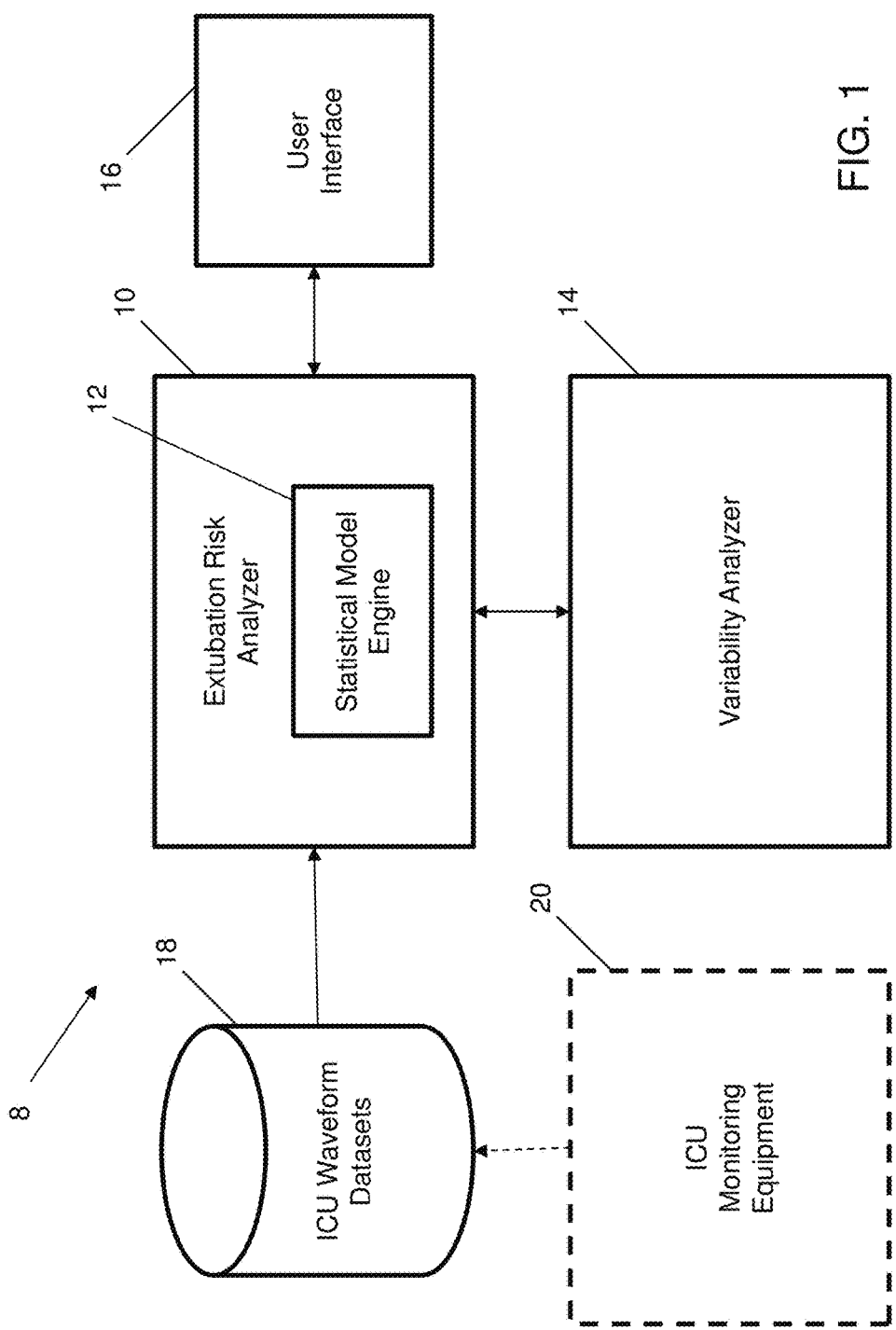
FIG. 1 is a schematic diagram of an example system for providing multi-organ variability decision support for extubation management.

It will be appreciated that for simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will also be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

The following enables extubation management to be improved, by providing clinicians with a system to support their decisions related to extubation. The system is based on the use of single or multi-organ variability, extracted from physiological waveforms acquired in ICUs. In particular, those waveforms undergo a phase of cleaning, event series extraction (e.g. R-R interval, inter-breath interval), and quality estimation (e.g., by applying techniques described in co-pending PCT Patent Application No. PCT/CA2013/050681 filed on Sep. 5, 2013 and entitled: "Method for Multi-Scale Quality Assessment for Variability Analysis", the contents of which are incorporated herein by reference and further details of which are provided below and shown in FIGS. 7 to 9). High quality event series may then be used to compute a variety of single-organ and multi-organ variability measures (e.g., see: (10) Bravi, A., Longtin, A. & Seely, A. J. E. Review and classification of variability analysis techniques with clinical applications. *Biomedical Engineering Online* 10, (2011)), through a windowed analysis.

It will be appreciated that a "variability analysis over time" or a "variability analysis" in general, will hereinafter refer to the computation of a measure of variability for a plurality of time intervals for each patient parameter, variable, organ etc. Each measure of variability is indicative of a degree and character to which a respective patient parameter changes over an interval of time, and each variability analysis enables changes in variability of the patient parameter to be observed over a period of time. A variability analysis as herein described can be performed on one or more patient parameters, i.e. single parameter and/or multi-parameter (e.g. single-organ or multi-organ), and the multiple measures of variability can be obtained according to any suitable pattern such as intermittent, continuous, etc.

Characteristic of the system described herein, is the ability to integrate variability measures with or without additional clinical information, to provide patient-specific indices related to:

1) a risk of failing extubation.
2) a probability of passing extubation.
3) SBT readiness, i.e. indicating to the clinician when is time to perform a SBT on a patient expected to be in proper conditions for extubation.
4) SBT failure, i.e. indicating to the clinician when to stop the SBT on a patient which is expected to fail extubation.

The visualization of one or multiple indices is context-specific, and in particular depends on the assistance needed by the clinician for a given patient.

The ability to provide these indices for a new patient may be based on statistical models created using previously collected data from patients who failed, and from patients who passed, extubation. The presented statistical models in the examples described herein are based on an ensemble averaging of logistic regressions, but may also include other types of generalized linear models, fuzzy c-means clustering, artificial neural network, multilayer perceptron, radial basis function network, support vector machines, decision trees, random forests, and Bayesian classifiers, as well as other types of ensembles, such as boosting, adaptive boosting and bagging.

Figure 3:
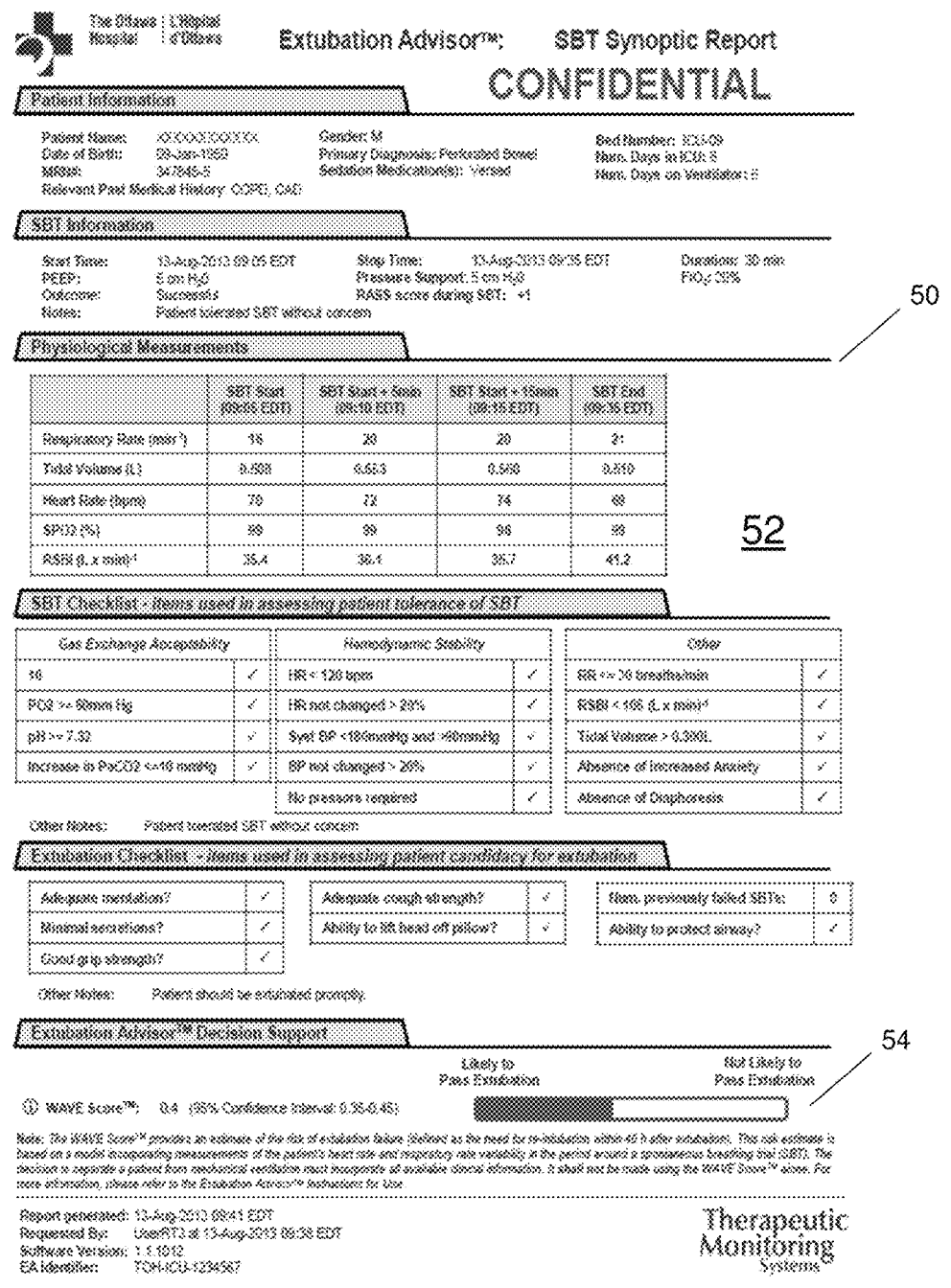

The clinically relevant variables used by the models are selected through optimization methods, such as brute force, grid search, greedy algorithms, Monte-Carlo methods, genetic algorithms, ant colony optimization. Cross-validation procedures such as leave-one-out, k-fold cross validation, and random resampling are used in combination with optimization methods for the identification of the models and their parameters. The indices generated by the system described herein may be presented together with additional clinical information, such as standard of care measures and checklists, to assist the clinical decision, e.g. as shown in FIG. 3 described below.

Turning now to FIG. 1, a system 8 is shown, which includes an extubation risk analyzer 10. The analyzer 10 includes or otherwise has access to a statistical model engine 12 for generating and selecting from statistical models and for performing other modelling operations. The analyzer 10 also includes or has access to a variability analyzer 14, which may be located remotely therefrom. It can be appreciated that the analyzer 10 may be communicable with multiple variability analyzers 14. A user interface 16 is also shown, which enables inputs to be received, and outputs to be provided by, the analyzer 10. The user interface 16 may include any one or more input/output mechanisms and may present a graphical user interface, e.g., via a browser. It can be appreciated that the analyzers 10, 14 and user interface 16 may be implemented by or provided on any suitable electronic device, including desktop and laptop computers, smart phones, tablets, consoles, integrated into in-clinic or in-hospital monitoring systems, etc.

The analyzer 10 also includes or has access to an ICU waveform dataset database 18 storing waveform data utilized by the system 8. The ICU waveform datasets in the database 18 may originate from various sources, including ICU-based monitoring equipment 20, which may also be included in or be accessible to the system 8 (as illustrated in dashed lines). It can be appreciated that various platforms and architectures may be employed, including local and wide area network, open and closed systems, local and cloud-based storage and processing, etc.

Figure 2:
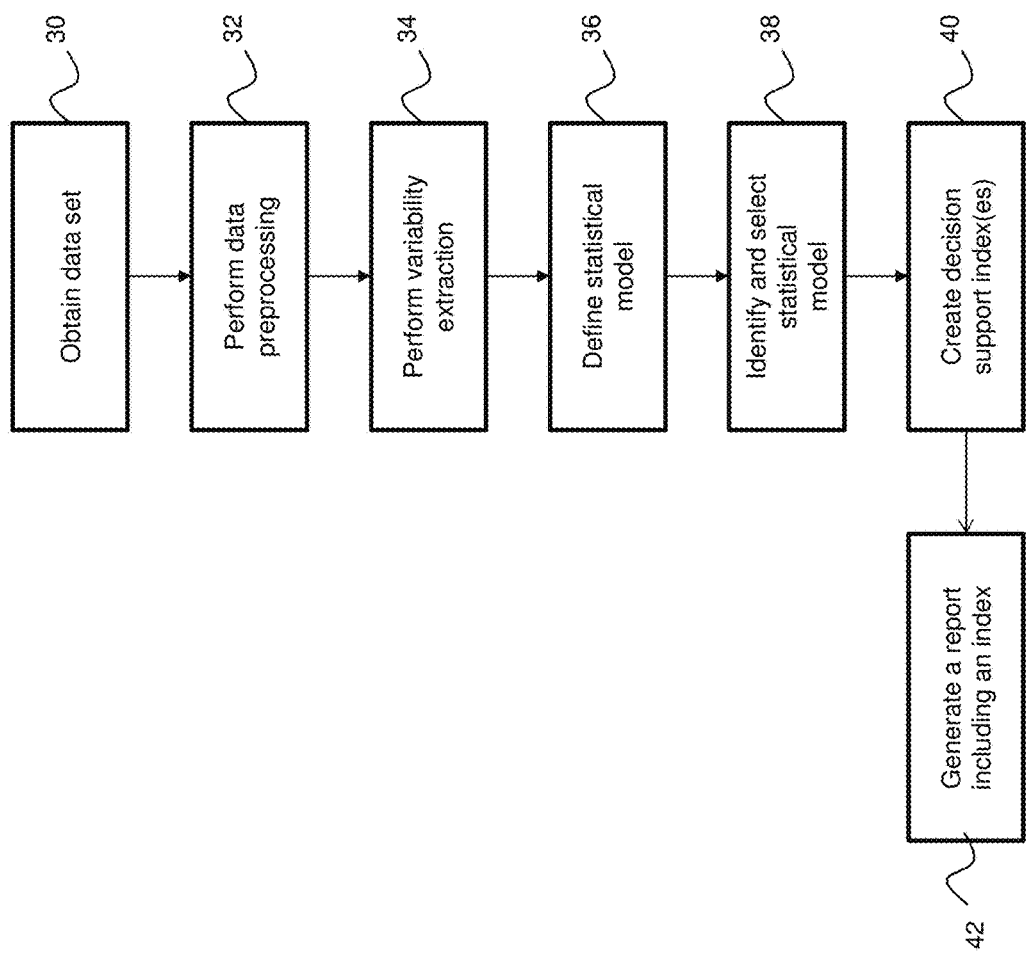
FIG. 2 is a flow chart illustrating example computer executable operations that may be performed in providing multi-organ variability decision support for extubation management.

FIG. 2 illustrates example computer executable operations that may be performed in providing multi-organ variability decision support for extubation management, as will now be described.

Dataset

The decision support system 8 for the management of extubation is based on an ensemble of logistic regressions, trained through a dataset from the database 18, including electrocardiographic and capnograph waveforms recorded from ICU patients who failed and who passed extubation, etc. At 30, such a dataset is obtained by the system 8.

Data Preprocessing

After cleaning the electrocardiograms (EKGs) and capnograms (expCO2) from artifacts, two event time series are created by conducting preprocessing at 32, e.g.: 1) the time elapsed between two successive R peaks of an EKG, and 2) the time elapsed between two successive expirations from an expCO2.

Variability Extraction

From the event time series, a set of measures of heart rate variability (HRV) and measures of respiratory rate variability (RRV) are extracted and tracked over time at 34, through a windowed analysis (e.g., 5 min window size for HRV, 15 min window size for RRV, 2.5 min window step for both).

Then, the median value for each measure of variability is computed on two time intervals, from, for example, 30 minutes prior the time of the SBT to the SBT time (called Pre-SBT), and from the SBT time to, for example, 30 minutes after (called During-SBT).

Statistical Model Definition

Given the median variability in Pre-SBT and During-SBT for both Passed and Failed extubation, a multivariate ensemble averaging of logistic regressions is created at 36. A logistic regression is a linear model which provides as output the probability of failing extubation; being mono-dimensional, the output of each logistic regression alone provides an indication of the probability of failing extubation, estimated by looking at only one measure of variability. The ensemble averaging comprising taking the output of N logistic regressions and averaging the output, so as to obtain a final probability. It may be noted that this process may be considered analogous to asking multiple independent "experts" to provide how confident they are that a given patient will either fail or pass extubation, and take a final decision integrating all the partial decisions.

Statistical Model Identification

The measures of variability to be included in the ensemble, as well as the optimal thresholds used by the logistic regressions to separate between "Passed" and "Failed", are selected at 38 based on a repeated random sub-sampling cross-validation. For example, an equal subset of the Passed and Failed population are randomly extracted from the whole sample to train the model, and the rest of the data is used to test its performances; in particular, a Receiver Operating Characteristic (ROC) curve is extracted, and the ROC Area under the curve (AUC) is computed. The process is then repeated a number of times (e.g. 1000), each time training the statistical model with a subset of the data and testing it on the remaining data, thus creating a distribution of ROC AUC values. A greedy approach repeating the presented procedure is used to select the variability measures which constitute the ensemble maximizing the median ROC AUC.

Decision Support Indexes Creation

Decision support indices are then created at 40. The output of the ensemble may be referred to herein as a "WAVE" score. The WAVE score can be used in multiple ways, depending on the targeted use.

Estimate Risk of Failing Extubation.

This index is evaluated at the end of an SBT. The WAVE score is transformed into the fold increase in risk of failing extubation by dividing it in ranges, and computing for each range the likelihood that a patient with that WAVE score is going to fail extubation.

Estimate the Probability of Passing Extubation.

This index is evaluated at the end of an SBT. The WAVE score is transformed into the fold increase in chances of passing extubation by dividing it into ranges and computing, for each range, the likelihood that a patient with that WAVE score is going to pass extubation.

Estimation of SBT Readiness.

This index is applied to patients being monitored in the ICU, and is based on a WAVE Score extracted from Pre-SBT only variability. The WAVE score is tracked continuously over time, and when its value approaches with a given confidence the value characterizing the Passed population, the patient is required to perform an SBT, for the final judgment of extubation readiness.

Estimation of SBT Failure.

This index is applied to patients performing an SBT. The WAVE score is tracked continuously over time, and when its value approaches with a given confidence the value characterizing the Failed population, the patient is required to stop the SBT, so to avoid further unnecessary stress.

Bedside Application of WAVE Score

The assistance to the clinical decision is provided by presenting WAVE scores in combination with additional standard of care measures and tools, such as checklists and reference tables. This combination of variability-dependent and variability-independent clinical information provides the clinician with heterogeneous patient-specific information, enabling a better extubation management. For example, as shown in FIG. 2, a report or checklist or table may be generated at 42 which includes at least one index or WAVE score.

FIG. 3 illustrates an example of an SBT Synoptic Report 50, which includes various clinical information 52 such as patient information, SBT information, physiological measurements, an SBT checklist (i.e. items used in assessing patient tolerance of SBT), an extubation checklist (i.e. items used in assessing a patient's candidacy for extubation). Included in this report 50 is a decision support portion 54, which in this example provides a WAVE score in a visually distinguishable bar chart that indicates whether or not the particular patient is likely to pass extubation, thus providing a meaningful visual reporting feature directly within the report 50, along with important clinical information.

The process of determining the risk or probability may therefore be used to yield a Synoptic SBT Report of the SBT, that uses a standardized process for evaluating patients along with standardized checklists for evaluating readiness for extubation. In other words, the overall measure of risk or probability, which depends on clinical factors and variability (one or more organ systems), can be displayed along with a synoptic report which presents the best of the standard clinical factors along with variability and the WAVE score, and all data is derived from a standardized assessment (ie fixed vent settings, sedation, analgesia) and data collection (i.e. what data and when is collected) process during the SBT.

The system 8 described herein therefore provides multiple indices for decision support for extubation management. Multi-organ variability monitoring, summarized into a multivariate ensemble predictive WAVE score offers added value to the standard of care available clinical information. By providing a better measure of the likelihood of extubation failure or success, the WAVE score has the potential help clinicians better identify when is not safe to extubate a patient (and thereby reducing the number of extubation failures associated with higher mortality, costs, and length of stay), as well as provide greater confidence to clinicians to better identify when it is safe to extubate, potentially at an earlier time point in the ICU (thereby leading to earlier extubation, and shorter length of stay). Notably, the system 8 described herein represents an intelligent system for decision support addressing the problem of extubation outcome prediction.

Obtaining Variability Measures

As discussed above, the extubation risk analyzer 10 may be used in conjunction with individual variability measures and analyses to provide decision support indices, e.g. along with an SBT synoptic report 50 as shown in FIG. 3. As such, the generation of such decision support indices and WAVE scores can be applied in any context in which variability measures, obtained from a variability analysis component 14', can be applied. For example, support indices can be generated using data obtained in real-time, previously obtained data, data obtained in an intensive care unit (ICU), data obtained using portable monitoring devices recording variability, etc. For example, data can be summarized in a mathematical model, which is then used for the computation of quality. A quality assessment of variability therefore is not dependent on any particular mechanism for obtaining the variability data, so long as a set of variability measures is available, and a quality measure can be obtained, as explained in greater detail below. The following illustrates three exemplary monitoring sites 111 (e.g., 111a, 111b, 111c) to demonstrate the various ways in which the variability measures can be obtained in order to generate a quality assessment. Further detail concerning an underlying software framework for obtaining and distributing variability data can be found in applicant's co-pending U.S. patent application Ser. No. 12/752,902, published under US 2010/0261977 and issued as U.S. Pat. No. 8,473,306 to Seely, the entire contents of which are incorporated herein by reference.

Figure 4:
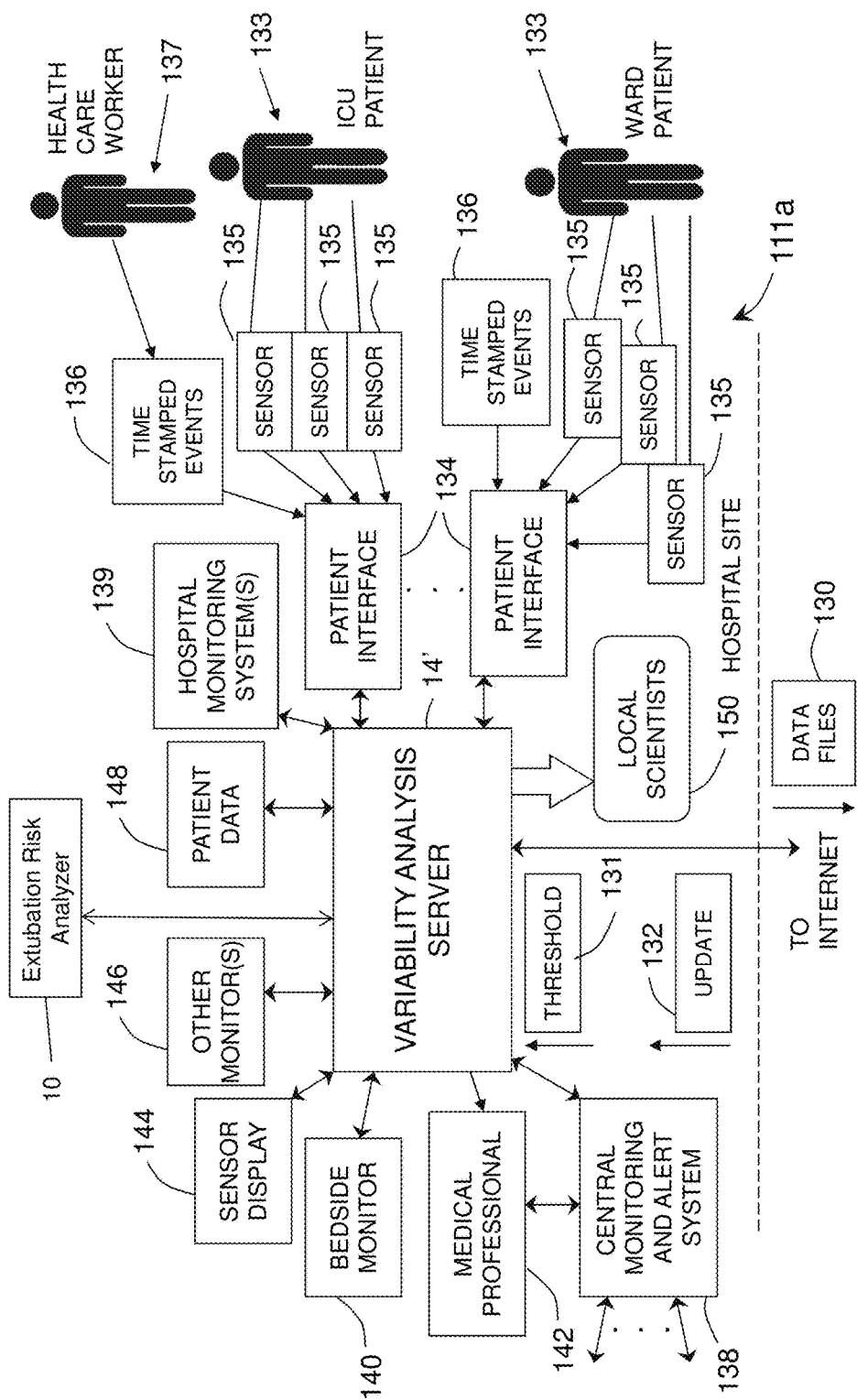
FIG. 4 is a block diagram of a hospital site including a variability analysis server having a quality module.

An example of a hospital monitoring site 111a is shown in FIG. 4. The elements shown in FIG. 4 are meant to illustrate several possible components that may interact with one another at the hospital site 111a, however, any number (or all) of these elements can be used or not used in specific hospital sites 111a depending on the actual equipment and/or personnel present at the hospital site 111a and the needs of the patients 133 and personnel. In addition, the parameters being monitored (and the monitors themselves) may differ from network to network. As will be explained, at each monitoring site 111, including the hospital site 111a shown in FIG. 4, is at least one variability analysis server 14' for using acquired data to conduct variability analyses over time and generate data files 130 that can be viewed at the site and provided to, for example, a central service (not shown). The variability analysis server 14' includes or otherwise has access to an extubation risk analyzer 10. As shown, each variability analysis server 14' can interface with multiple patients 133 and, as such, typically only one variability analysis server 14' is required at each monitoring site 111. The variability analysis server 14' gathers data acquired from one or more patients 133 through individual patient interfaces 134, computes the measures of variability (i.e. conducts variability analyses) for one or more patient parameters, and connects to, for example, a central server through the Internet, for facilitating the transfer and/or receipt of data files 130, threshold data 131 and update data 132. As shown, there can be different types of patients 133 such as those in the ICU or in a regular hospital ward.

The patient interfaces 134 monitor physiological parameters of the patient 133 using one or more sensors 135. The data or patient parameters can include any variable that can be accurately measured in real time or intermittently. The data may be obtained from a continuous waveform (at a certain frequency level, e.g. 100 Hz for a CO2 capnograph or 500 Hz for an EKG), or taken as absolute measurements at certain intervals, e.g. temperature measurements. The sensors 135 and patient interfaces 134 may include, for example, an electrocardiogram (ECG), a $CO_2$ capnograph, a temperature sensor, a proportional assist ventilator, an optoelectronic plethymography, a urometer, a pulmonary arterial catheter, an arterial line, an $O_2$ saturation device and others. To provide more meaning to the data acquired through the sensors 135, clinical events are associated with the data, through an act of recording time stamped events 136, which are typically entered by a heath care worker 137 in the hospital (bedside) environment. Clinical (time stamped) events can be physical activity, administration of medication, diagnoses, life support, washing, rolling over, blood aspiration etc. The clinical events are associated with a specific time, which is then also associated with the data that is acquired at the same specific time using the sensors 135. It will be appreciated that the clinical events can also be recorded in an automated fashion, e.g. by utilizing algorithms which detect events electronically and process such events to designate them as clinical events or noise. In this example, the patient interface 134 is configured to gather the time stamped event data 136 concurrently with the sensor data 135, further detail being provided below. It may be noted that additional non-time-stamped information (e.g. demographics) can also be recorded for each patient.

As can be seen in FIG. 4, the variability analysis server 14' not only connects to the patient interfaces 134 and the Internet, but also to several other components/entities within the hospital site 111a. For example, the server 14' can interface with a hospital monitoring system 139 such as a nurse's station, as well as a central monitoring and alert system 138. The central monitoring and alert system 138 is capable of monitoring the variability analyses performed by the variability analysis server 14' in order to detect critical or potentially critical situations evident from such variability analyses and provide an alert or alerts to a medical professional 142, who can also receive data directly from the variability analysis server 14'. The variability analysis server 14' can be embodied as a fixed unit or a moveable unit such as on a cart, in order to facilitate movement about the hospital site 111a to serve multiple patients 133 in multiple locations. Similarly, the variability analysis server 14' can be a proprietary apparatus or can be embodied as an add-on to existing beside or centralized equipment to minimize space.

The variability analysis server 14' can also interact with a bedside monitor 140, which may be made available to or otherwise represent a nurse or other personnel that monitors the patient 133 at the bedside. Similarly, the variability analysis server 14' can also interact with sensor displays 144, which are associated with other medical equipment such as ECGs, blood pressure sensors, temperature sensors etc. As noted above, the variability analysis server 14' can be a separate, stand-alone unit but may also be integrated as a plug-in or additional module that in this case could be used or integrated with existing bedside monitoring equipment, displays and sensors. FIG. 4 also shows other monitors 146 which can include any other monitoring system or equipment that either can provide useful medical data or patient data 148 or would benefit from the data acquired by the variability analysis server 14'. Patient data 148, e.g. provided by an electronic patient database (not shown) or manually entered can also interact with the variability analysis server 14'. As will be discussed below, the patient data 148 may be appended to, or included with the data files 130 to provide further context for the data contained therein. This enables patient specifics such as age, general health, sex etc. be linked to the acquired data to assist in organizing data into demographics. As also shown in FIG. 4, the variability analysis server 14' can provide data or otherwise useful information for local scientists 150 that are interested in or involved in the implications and effects of variability. It will be appreciated that patient privacy and other concerns can be addressed as required, by adding data security or other de-identification measures.

Figure 5:
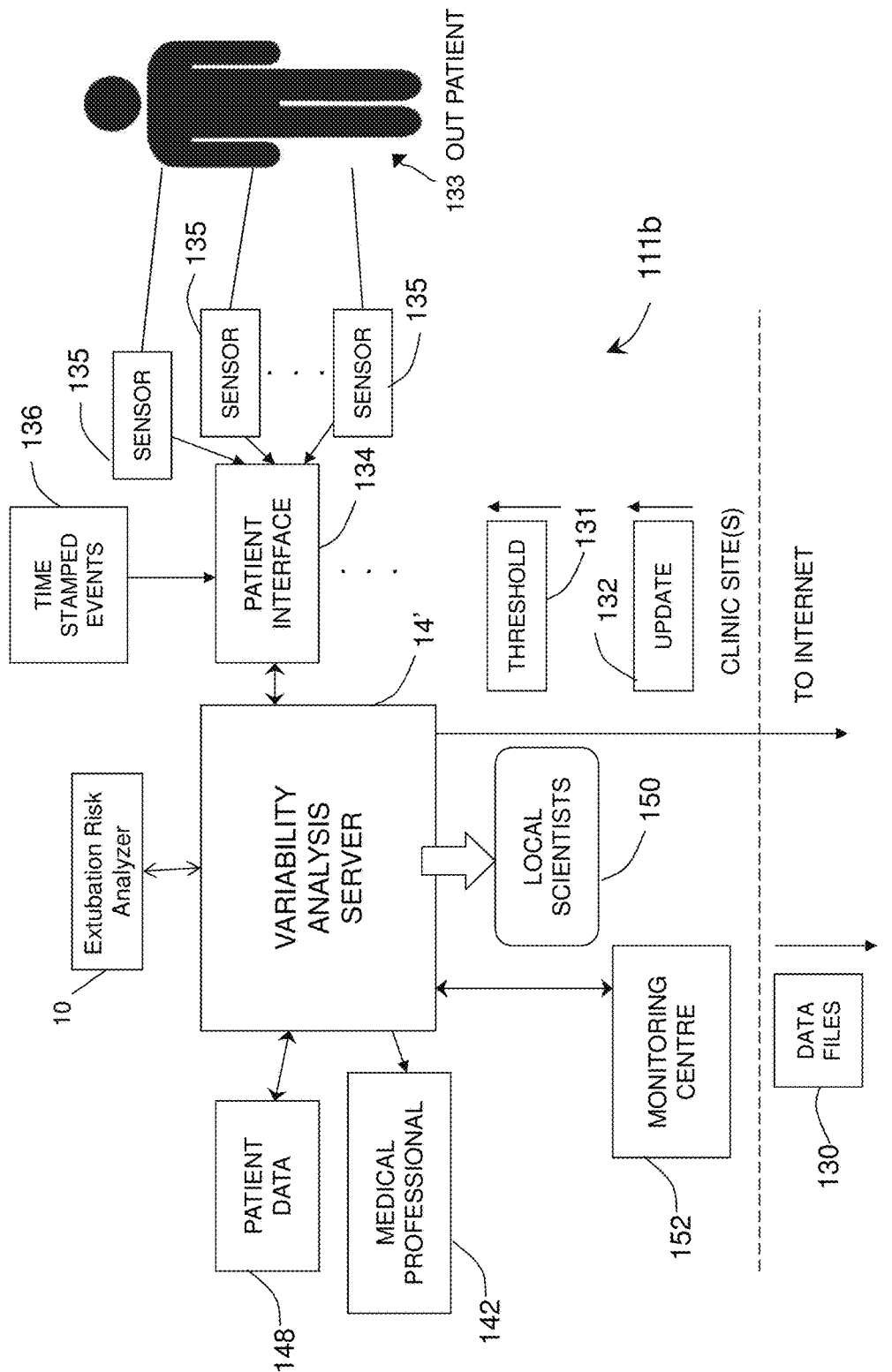
FIG. 5 is a block diagram of a clinic site including a variability analysis server having a quality module.

Turning now to FIG. 5, a clinic site 111b is shown. An example of a clinic site 111b is a bone marrow transplant clinic. Similar to the hospital site 111a discussed above, the clinic site 111*b* includes a variability analysis server 14', that obtains data from one or more patient interfaces 134, and connects to the Internet for facilitating data transfer (i.e. to send data files 130 and to receive threshold data 131 and update data 132). In the clinic site 111*b*, the patients 133 are referred to as outpatients as they are not admitted to a hospital. The sensors 135, clinical events recorded as time stamped events 136 and patient data 148 is acquired and used in a manner similar to that discussed above and thus further details need not be reiterated. Similarly, the variability analysis server 14' can provide data and interact with medical professionals 142 at the clinic site 111*b*, as well as local scientists 150, if applicable. The clinic site 111*b* may include one or more variability analysis servers 14', and would typically include a monitoring center 152 that monitors the analyses of the various outpatients 133 and provides alerts if necessary. The monitoring center 152 enables the clinic's variability analysis server 14' to be monitored from a remote location and allows personnel to monitor several servers 14' if several are present in the clinic. In this way, a central monitoring center 152 can be used to service several clinic sites 111*b*.

Figure 6:
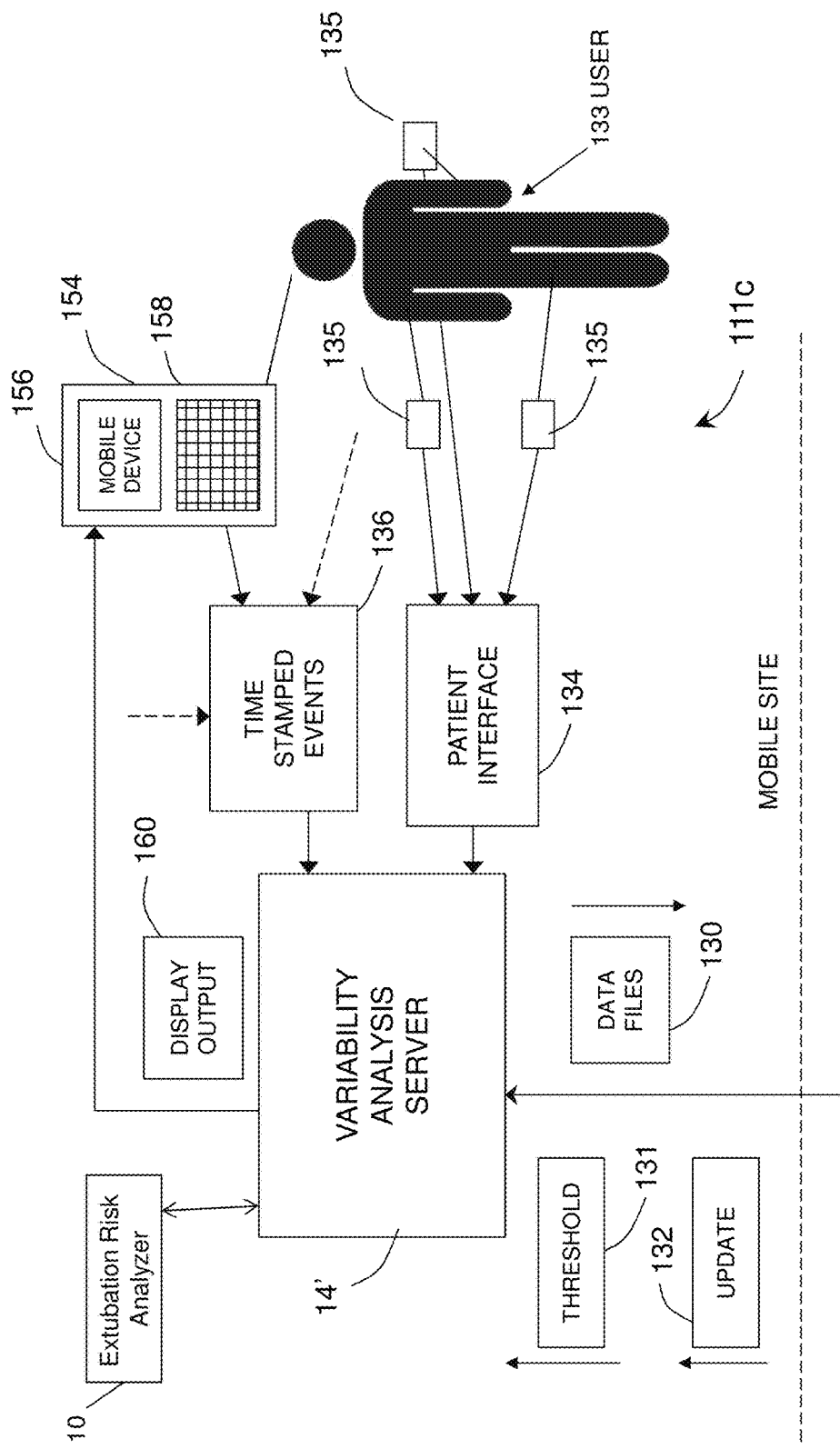
FIG. 6 is a block diagram of a mobile site including a variability analysis server having a quality module.

A mobile site 111*c* is shown in FIG. 6. The mobile site 111*c* enables the capabilities of the variability analysis server 14' to be used outside of the hospital and clinical environments and, as such, in this embodiment, the mobile site 111*c* serves any "user" or "subject". For the sake of consistency, hereinafter the term "patient" will refer collectively to any user or subject. In this way, it may be appreciated that variability analyses can be performed on any user, including athletes, firefighters, police officers, or any other person that can benefit from monitoring variability of one or more physiological parameters. This can therefore extend to providing real-time monitoring in extreme environments such as during a fire, in a mine, during rescue missions etc. where variability can indicate a potentially critical situation. In all cases, variability can be monitored over time and analyzed on an individual basis for any patient 133 such that the resultant data is specific to that individual. Using the wider system allows a central service to take advantage of the individual results for many patients 133 and ascertain further and more complete information. The mobile site 111*c* generally represents any site that includes a variability analysis server 14', which connects to the system 8 and can communicate with one or more patients 133, whether they are patients in the traditional sense or another type of user.

In the example shown in FIG. 6, the user 133 generally includes a mobile device 154 and has a number of sensors 135 that are in communication with a variability analysis server 14'. The mobile device 154 can also be used to provide inputs, e.g. for the time stamped event data 136, as well as to provide a display to the user 133 for entering parameters or to view display data 160 acquired by the sensors 135 and/or processed by the server 14'. The connections between the mobile device 154 and the server 14', as well as between the sensors 135 and patient interface 134 can be wired or wireless and the variability analysis server 14' can be a fixed unit at a base station or a portable unit such as on a cart at a monitoring center. The mobile device 154 can be a personal digital assistant (PDA) or smartphone, mobile telephone, laptop computer, tablet computer, personal computer, or any other device that can provide an input device, a display and some form of connectivity for interacting with the variability analysis server 14', preferably in a completely mobile manner.

As noted above, each monitoring site 111 may include a variability analysis server 14'. Details of various embodiments of existing variability analysis apparatus and configurations can be found in U.S. Reissue Pat. No. RE41,236 E to Seely, the entire contents of which are incorporated herein by reference.

Variability Quality

Physiological waveforms are now harvested at the bedside and manipulated to provide informational and decisional data points for clinicians and caregivers. For example, the study of heart rate variability (HRV) which is derived from the electrocardiogram (ECG) has benefited from nearly two decades of research and its applications in clinical practice are wide ranging. HRV is widely studied and used as a marker of illness severity.

Variability analysis measures the complexity of a time series of event occurrences, such as heart beats or breaths. As discussed above, assessing the quality of the events, and the underlying waveform from which the events are derived is important to validate the subsequent interpretation of the variability measurements. The quality of the variability measurements themselves is also important in providing confidence in the reported values.

Figure 7:
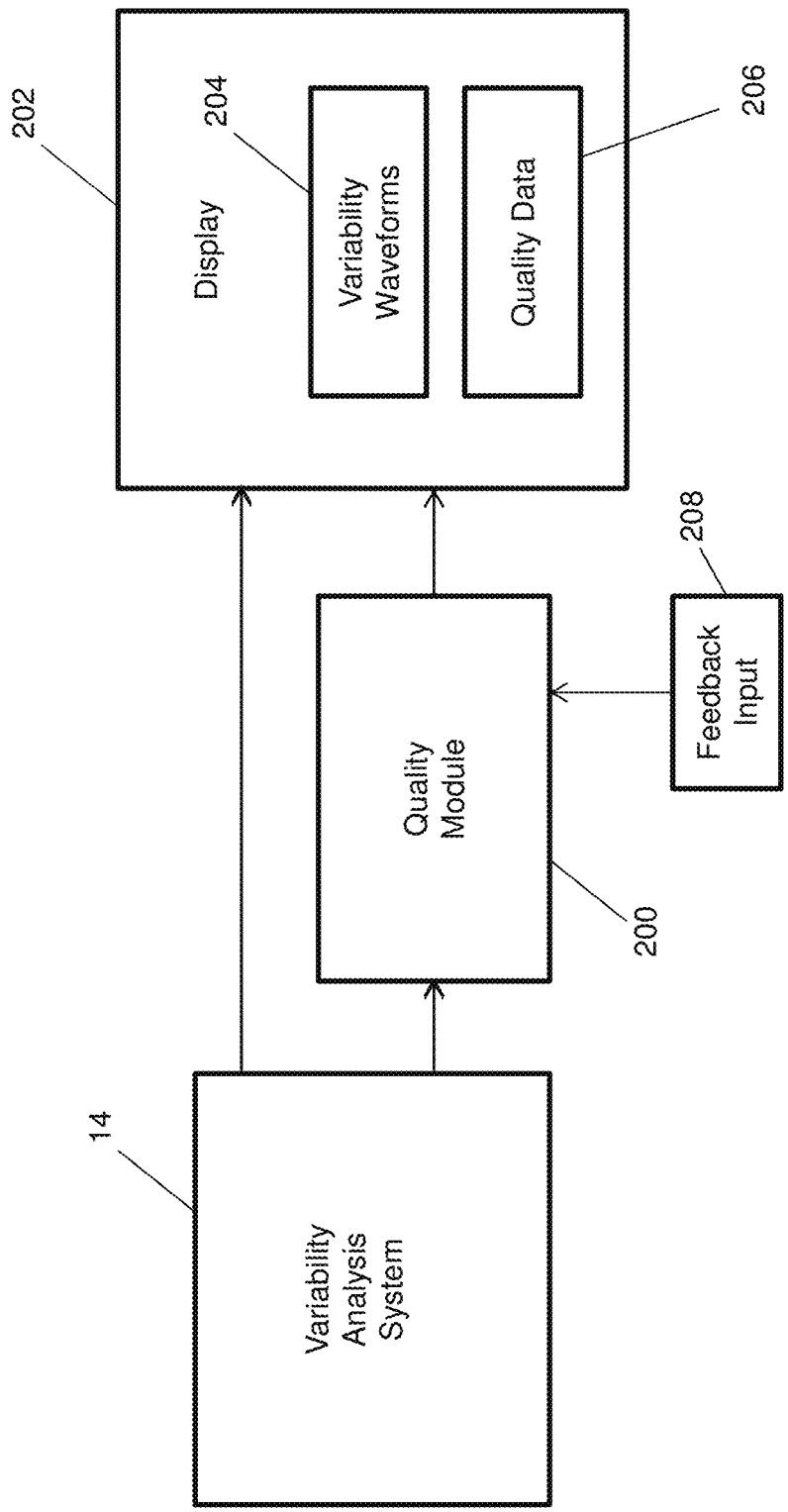
FIG. 7 is a block diagram illustrating the incorporation of quality measurements into a variability analysis.

FIG. 7 illustrates a variability monitoring/analysis environment in which a quality module 2000 is incorporated into or otherwise coupled to or integrated with a variability analysis system 14. Through this integration with the variability analysis system 14, the quality module 200 can generate quality data 206 (e.g., reports, measures, etc.) that can be displayed along with variability waveforms 204 on a display 202 of a computing system. For example, such a quality analysis can be performed in conjunction with a variability analysis performed in connection with an extubation decision support process as described above.

The quality module 200 may also be configured, as shown in FIG. 7, to receive feedback input 208, such as user assessments of the quality of a particular variability waveform, interval or individual measurement, which can enhance the quality data 206.

It can be appreciated that the components in FIG. 7 are shown in isolation for illustrative purposes only and such components may be configured in different arrangements. For example, the components shown in FIG. 7 may be integrated into a single computing device or may operate within a distributed or otherwise networked system, and may also be further integrated with an extubation risk analyzer 10.

The present quality assessment therefore includes a modular framework for the analysis of a generic physiological waveform, and may also include event and stationarity assessments to prepare a high quality event time series for a variability analysis, and to measure the quality of the reported variability measures. The overall quality of the window can be reported as an index which summarizes the quality of the data at each step in processing. The framework described herein is also applied to the capnogram which is one embodiment of the method.

Figure 8:
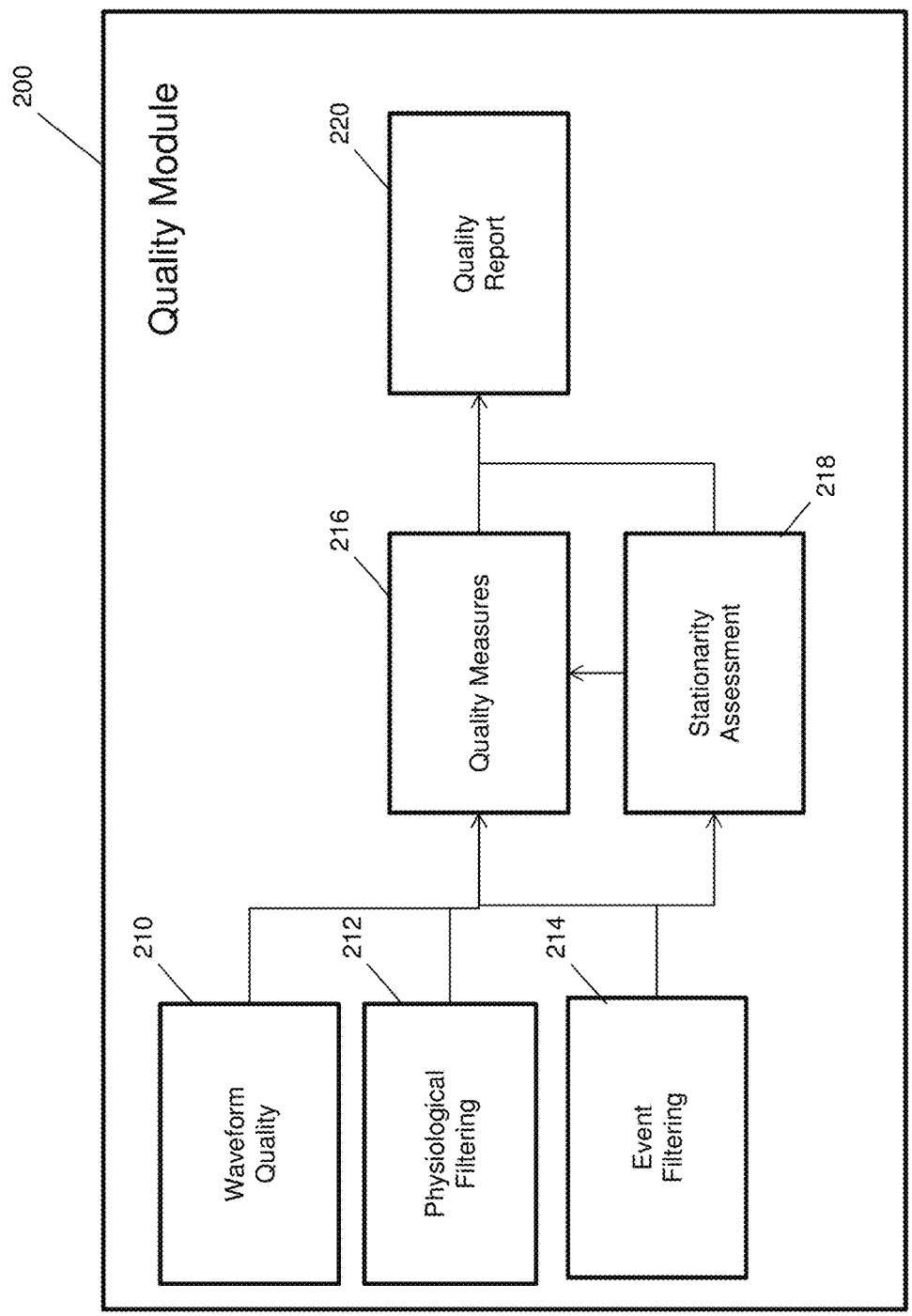
FIG. 8 is a flow diagram illustrating a process for quality assessment.

FIG. 8 illustrates further detail of a configuration for the quality module 200. In the example shown in FIG. 8, the quality module 200 performs a waveform quality stage 210, a physiological filtering stage 212, and an event filtering stage 214, all of which feed into a stationarity assessment 218 and a quality measures stage 216. The quality measures and stationarity assessments are then fed into a quality report stage 220, which reports on the quality of the variability waveforms being displayed, to enhance the data conveyed by such waveforms.

The following provides a quality assessment, addressing specific concerns for variability analysis. One embodiment uses the end tidal CO2 signal as an input waveform presented in section III.

The quality stages shown in FIG. 8 may be specifically designed for the purpose of variability analysis conducted over time as is its application to the capnogram signal. These quality stages can be used to ensure events used for variability calculations are of high quality and exhibit stationary behavior over a suitable period of time. The quality stages can be used to estimate the quality of the signal (i.e. level of noise and artifacts such as disconnections, saturation, baseline wandering, motion artifacts, etc.), and to exclude from the analysis segments of the signal that are of poor quality (thereby not enabling a proper computation of the event time series). A particular concern of stationarity which is assessed in the stationarity assessment stage 218, and which is of great importance for variability, is also addressed with these quality stages. It may be noted that in its simplest form, stationarity is the property of having stable statistical moments. It is recognized that a requirement for many popular techniques of time series analysis, including complexity of the variability measures. Without stationarity, interpreting the measures with confidence may be challenging (see R. Manuca and R. Savit, "Stationarity and nonstationarity in time series analysis," *Physica D*, vol. 99, pp. 134-161, 12/15. 1996).

In a variability analysis, variability is calculated over time on the high quality event time series, usually on a plurality of windows, which may overlap. A quality assessment for variability may also be provided for variability measures calculated in time periods surrounding a clinical event. Therefore combining the waveform and event quality measures over a window provides a more complete quality assessment. The diagram of the assessment is presented in FIG. 8, and a detailed representative diagram for the quality assessment as it is integrated with the variability analysis, is presented in FIG. 9. In FIG. 8, as noted above, the processing stages include assessing the quality of the input waveform to identify segments which are suitable for segmentation into events. Following the segmentation into events, these events are stratified into three categories: non-physiological event, physiological events, and high quality events. Multiple methods for this stratification are described in section II.

Figure 9:
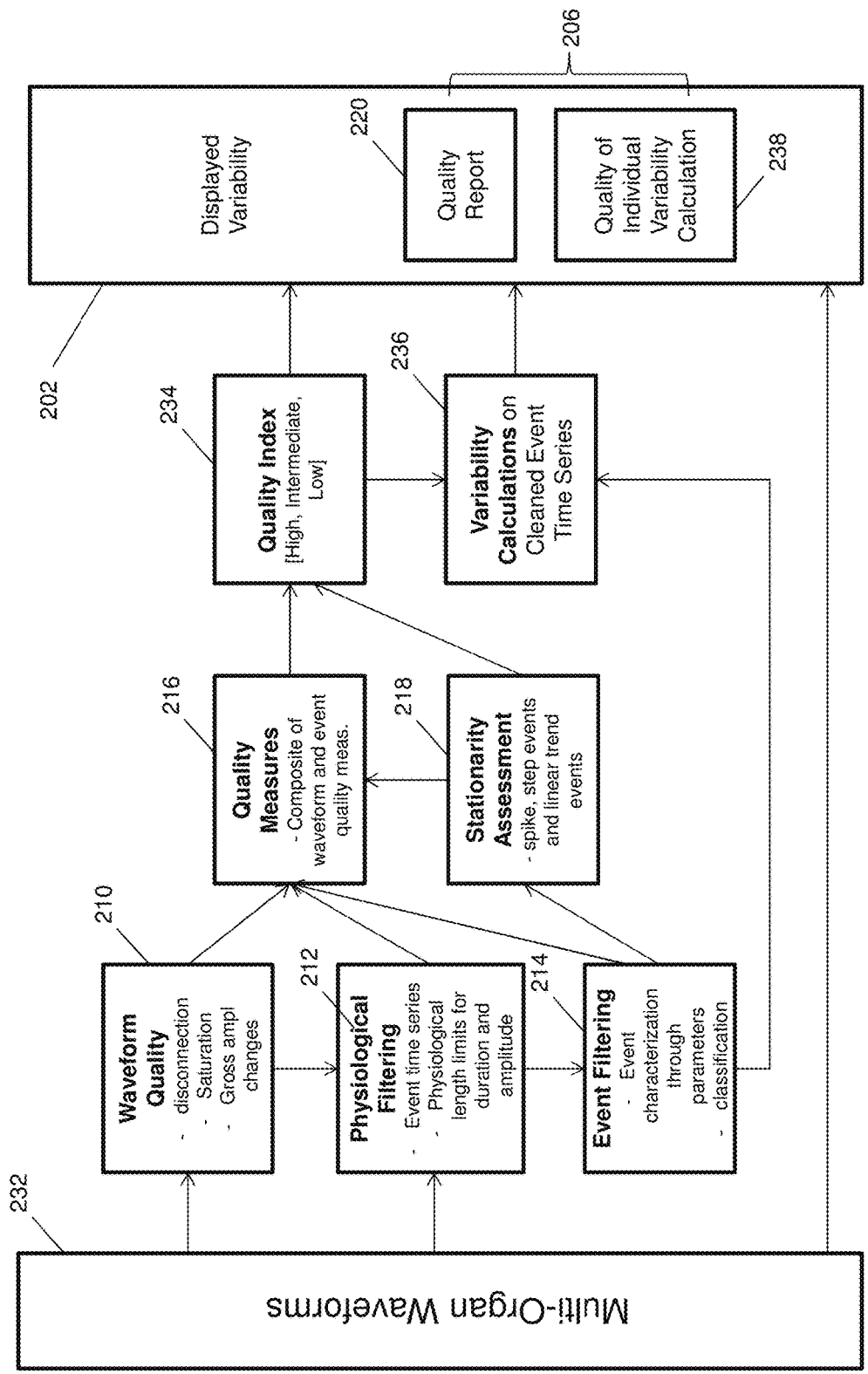
FIG. 9 is a representative diagram of quality framework for variability quality assessment.

As illustrated in FIG. 9, using time intervals (windows), the high quality event time series is assessed for stationarity in the stationarity assessment stage 218. The stationarity assessment stage 218 has been found to be important for variability measurements. Data obtained from the initial processing stages (waveform quality stage 210, physiological filtering stage 212, event filtering stage 214, and stationary assessment stage 218) are used to create quality measures in the quality measures stage 216. The quality measures are related to both a window (or interval) and to the individual variability measurements within that window. The quality measures may be implemented using a machine learning model (e.g. using neural networks, etc.) to optimally combine waveform, event, physiological and stationarity information. These measures provide information to the clinician about the underlying waveform and event time series, and about the quality of the measurements; providing confidence about the interpretation. Measurements from low quality windows (e.g., low quality because of the waveform, event, stationarity or variability) may be chosen not to be displayed (either graphically or numerically). This assures clinicians that displayed information is at least of intermediate quality.

The quality index 234 is implemented optimally combining the quality measures and the stationarity information using a machine learning model (e.g. using decision trees). The quality index 234 is used to summarize the information from the quality measures into a simple metric which can be used by those clinicians uninterested in the finer details of the quality analysis. The quality report 220, derived from the quality assessment is linked, through a time stamp to the waveform, event and variability information and displayed on the display 202. In addition to the quality report 220, the quality of individual variability calculations 238 can also be displayed as shown in FIG. 9. If one variability measurement is selected on the display 202, the quality report 220 shown for that window can be used to call the waveform and event time series for that window. Similarly, selection of individual measures of variability can cause individual quality measures to be displayed. The physiological filtering 212 and event filtering 214 stages are used to annotate each event in that time series as one of the three categories mentioned above, allowing the clinicians to inspect the waveform and event annotations. The number of quality levels and threshold values on the quality measure to create is modular and can be changed for specific applications. For example, different stationarity requirements could be enforced for certain input types of event time series.

It can be appreciated that the framework described herein may be applied to any physiological waveforms including sets of multi organ waveforms such as the ECG and capnography waveforms which are produced by different organ systems yet are intrinsically related as measure by the cardiopulmonary synchrony (P. Z. Zhang, W. N. Tapp, S. S. Reisman and B. H. Natelson, "Respiration response curve analysis of heart rate variability," *IEEE Transactions on Biomedical Engineering*, vol. 44, pp. 321, April 1997). Amongst the two signals, only the ECG has a clearly defined physiological model and morphology and has been extensively studied (Electrophysiology, Task Force of the European Society of Cardiology the North American Society of Pacing, "Heart Rate Variability Standards of Measurement, Physiological Interpretation, and Clinical Use," *Circulation*, vol. 93, pp. 1043-1065, March 1996), and (S. Cerutti, A. L. Goldberger and Y. Yamamoto, "Recent Advances in Heart Rate Variability Signal Processing and Interpretation," *IEEE Transactions on Biomedical Engineering*, vol. 53, pp. 1, January 2006).

The capnogram has benefited from extensive documentation of tracings (B. Smalhout and Z. Kalenda, *An Atlas of Capnography.*, 2nd ed. The Netherlands: Kerckebosche Zeist, 1981). Prior to the widespread of powerful computers, analysis and measurements were done by hand (measuring angles, visual inspection of shape, and selection of individual breaths for classifiers and detectors), see (B. Smalhout and Z. Kalenda, *An Atlas of Capnography.*, 2nd ed. The Netherlands: Kerckebosche Zeist, 1981), and see (J. M. Goldman and B. H. Dietrich, "Neural network analysis of physiologic waveforms," in *Proceedings of the Annual International Conference of the IEEE Engineering in Medicine and Biology Society, Vol.* 13, 1991, pp. 1660).

Limitations of this method may include reproducibility, a reliance on experts with limited availability, and a limit to the number of analyses which may be conducted. To overcome this, the system described herein extends the knowledge gained from HRV and address the limitations in traditional capnograph processing to provide a complete quality assessment for generic physiological waveform inputs. The quality of the signal is ascertained at multiple levels of processing (waveform, events, stationarity), which are specific to variability analysis. The quality process applied to the end tidal $CO_2$ signal as an example of use in section III, and an example of quality report on the ECG is presented in section IV.

It will be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the risk analyzer 10, statistical model engine 12, variability analyzer 14, ICU waveform dataset database 18, or ICU monitoring equipment 20, or any component of or related thereto, or accessible or connectable thereto. Any application or module herein described may be implemented using computer readable/executable instructions that may be stored or otherwise held by such computer readable media.

The steps or operations in the flow charts and diagrams described herein are just for example. There may be many variations to these steps or operations without departing from the principles discussed above. For instance, the steps may be performed in a differing order, or steps may be added, deleted, or modified.

Although the above principles have been described with reference to certain specific examples, various modifications thereof will be apparent to those skilled in the art as outlined in the appended claims.

The invention claimed is:

1. A computer-implemented method for supporting extubation management, the method comprising:
accessing a waveform dataset database to obtain waveform data previously collected from a plurality of patients, the waveform data comprising waveforms associated with patients that experienced one of a plurality of extubation outcomes;
obtaining from one or more variability analyzers, waveform data and a plurality of variability metrics in a variability data set indicative of a degree and character to which at least one patient parameter changes over intervals of time for the plurality of patients;
computing a plurality of different predictive models using the variability data and the waveform data obtained from the database;
applying the waveform data and the variability data set for a corresponding patient to each of the plurality of predictive models to obtain a plurality of logistic regression predictive models indicative of an extubation outcome by selecting measures of variability from the variability data set and determining at least one threshold for determining the extubation outcome, each logistic regression providing a probability of the extubation outcome;
averaging the plurality of logistic regression predictive models to generate an ensemble average of logistic regression predictive models indicating a final probability of the extubation outcome; and
displaying via a user interface and/or outputting via a report, at least one decision support index determined from the ensemble of logistic regression predictive models that is indicative of the final probability of the extubation outcome, along with standard clinical factors for the corresponding patient, at least one of the standard clinical factors normally used to evaluate readiness for extubation, wherein the displaying is performed in a clinical location where the extubation is performed to assist in a clinical decision related to the extubation.

2. The method of claim 1, further comprising displaying with the at least one decision support index, additional information corresponding to a subject being analyzed.

3. The method of claim 1, wherein the at least one patient parameter comprises respiratory rate and heart rate.

4. The method of claim 1, wherein the at least one index comprises an index estimating a likelihood of failing extubation.

5. The method of claim 4, wherein the index estimating a likelihood of failing extubation is evaluated subsequent to a spontaneous breathing trial (SBT).

6. The method of claim 4, wherein the index estimating a likelihood of failing extubation is transformed into a fold increase in risk of failing extubation by computing for each of a plurality of ranges, a likelihood that the subject is going to fail extubation.

7. The method of claim 1, wherein the at least one index comprises an index estimating a likelihood of passing extubation.

8. The method of claim 7, wherein the index estimating a likelihood of passing extubation is evaluated subsequent to an SBT.

9. The method of claim 7, wherein the index estimating a likelihood of passing extubation is transformed into a fold increase in probability of passing extubation by computing for each of a plurality of ranges, a likelihood that the subject is going to pass extubation.

10. The method of claim 1, wherein the displayed user interface and/or report comprises an additional index estimating SBT readiness.

11. The method of claim 10, wherein the index estimating SBT readiness is applied to subjects being monitored in an intensive care unit (ICU), and is based on data extracted from pre-SBT only variability.

12. The method of claim 11, wherein the index estimating SBT readiness is tracked continuously over time, and when its value approaches with a given confidence the value characterizing a passed population, the subject is required to perform an SBT, for a judgment of extubation readiness.

13. The method of claim 1, wherein the displayed user interface and/or report comprises an additional index estimating SBT failure.

14. The method of claim 13, wherein the index estimating SBT failure is applied to subjects performing an SBT.

15. The method of claim 14, wherein the index estimating SBT failure is tracked continuously over time, and when its value approaches with a given confidence value characterizing a failed population, the subject is required to stop the SBT.

16. The method of claim 1, wherein the variability data set comprises multi-organ variability measures.

17. The method of claim 1, wherein the at least one index is combined with additional clinical information.

18. The method of claim 1, wherein the at least one index is combined with at least one of a standard of care tool, and a standard of care measure.

19. The method of claim 1, wherein the standard clinical factors comprise any one or more of: patient information, SBT information, physiological measurements, an SBT checklist, or an extubation checklist.

20. The method of claim 1, further comprising performing the extubation while the user interface and/or report are being displayed in the clinical location.

21. A non-transitory computer readable storage medium comprising computer executable instructions for supporting extubation management, the computer executable instructions comprising instructions for:
  accessing a waveform dataset database to obtain waveform data previously collected from a plurality of patients, the waveform data comprising waveforms associated with patients that experienced one of a plurality of extubation outcomes;
  obtaining from one or more variability analyzers, waveform data and a plurality of variability metrics in a variability data set indicative of a degree and character to which at least one patient parameter changes over intervals of time for the plurality of patients;
  computing a plurality of different predictive models using the variability data and the waveform data obtained from the database;
  applying the waveform data and the variability data set for a corresponding patient to each of the plurality of predictive models to obtain a plurality of logistic regression predictive models indicative of an extubation outcome by selecting measures of variability from the variability data set and determining at least one threshold for determining the extubation outcome, each logistic regression providing a probability of the extubation outcome;
  averaging the plurality of logistic regression predictive models to generate an ensemble average of logistic regression predictive models indicating a final probability of the extubation outcome; and
  displaying via a user interface and/or outputting via a report, at least one decision support index determined from the ensemble of logistic regression predictive models that is indicative of the final probability of the extubation outcome, along with standard clinical factors for the corresponding patient, at least one of the standard clinical factors normally used to evaluate readiness for extubation, wherein the displaying is performed in a clinical location where the extubation is performed to assist in a clinical decision related to the extubation.

22. An electronic device comprising a processor, and memory, the memory comprising computer executable instructions for supporting extubation management, the computer executable instructions comprising instructions for:
  accessing a waveform dataset database to obtain waveform data previously collected from a plurality of patients, the waveform data comprising waveforms associated with patients that experienced one of a plurality of extubation outcomes;
  obtaining from one or more variability analyzers, waveform data and a plurality of variability metrics in a variability data set indicative of a degree and character to which at least one patient parameter changes over intervals of time for the plurality of patients;
  computing a plurality of different predictive models using the variability data and the waveform data obtained from the database;
  applying the waveform data and the variability data set for a corresponding patient to each of the plurality of predictive models to obtain a plurality of logistic regression predictive models indicative of an extubation outcome by selecting measures of variability from the variability data set and determining at least one threshold for determining the extubation outcome, each logistic regression providing a probability of the extubation outcome;
  averaging the plurality of logistic regression predictive models to generate an ensemble average of logistic regression predictive models indicating a final probability of the extubation outcome; and
  displaying via a user interface and/or outputting via a report, at least one decision support index determined from the ensemble of logistic regression predictive models that is indicative of the final probability of the extubation outcome, along with standard clinical factors for the corresponding patient, at least one of the standard clinical factors normally used to evaluate readiness for extubation, wherein the displaying is performed in a clinical location where the extubation is performed to assist in a clinical decision related to the extubation.

* * * * *